United States Patent [19]
Bolduc et al.

[11] 4,182,328
[45] Jan. 8, 1980

[54] DISPENSING INSTRUMENT AND METHOD

[75] Inventors: Lee R. Bolduc, Clearwater, Fla.;
Eugene A. Dickhudt, New Brighton, Minn.

[73] Assignee: Population Research Incorporated, Clearwater, Fla.

[21] Appl. No.: 854,081

[22] Filed: Nov. 23, 1977

[51] Int. Cl.$^2$ ............................................. A61M 1/00
[52] U.S. Cl. ................................ 128/235; 128/349 B; 128/1 R
[58] Field of Search ............... 128/235, 260, 215, 216, 128/1 R, 349, 241, 246, 240

[56] References Cited
U.S. PATENT DOCUMENTS 3,972,331   8/1976   Bolduc et al. .................. 128/235 X Primary Examiner—John D. Yasko
Attorney, Agent, or Firm—Joseph F. Breimayer; Lew Schwartz; Richard O. Bartz

[57] ABSTRACT

A fluid dispensing instrument and method for placing a drug material into the canals of the Fallopian tubes of a female. The instrument has a housing carrying a piston and cylinder assembly. An elongated flexible tubular probe attached to the housing carries an expandable sleeve. The piston and cylinder assembly is operable to fully collapse the sleeve prior to insertion through the cervical opening into the uterine cavity. After the sleeve is inserted into the uterine cavity, an ampulla storing the drug material is loaded into the instrument. The piston and cylinder assembly is then actuated to initially partially expand the sleeve. Operation of the piston and cylinder assembly moves a plunger into the ampulla to dispense the drug material into the uterine cavity above the partly expanded balloon. The sleeve is then fully expanded to move the drug material from the uterine cavity into the canals of the Fallopian tubes.

35 Claims, 17 Drawing Figures

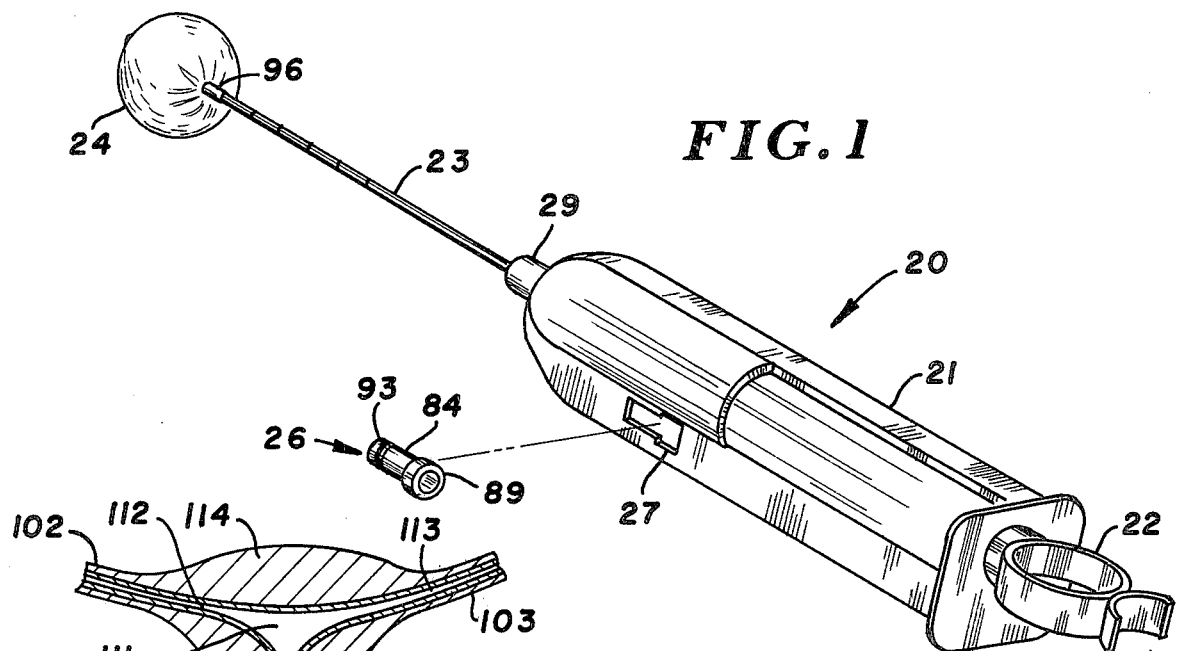
FIG. 1
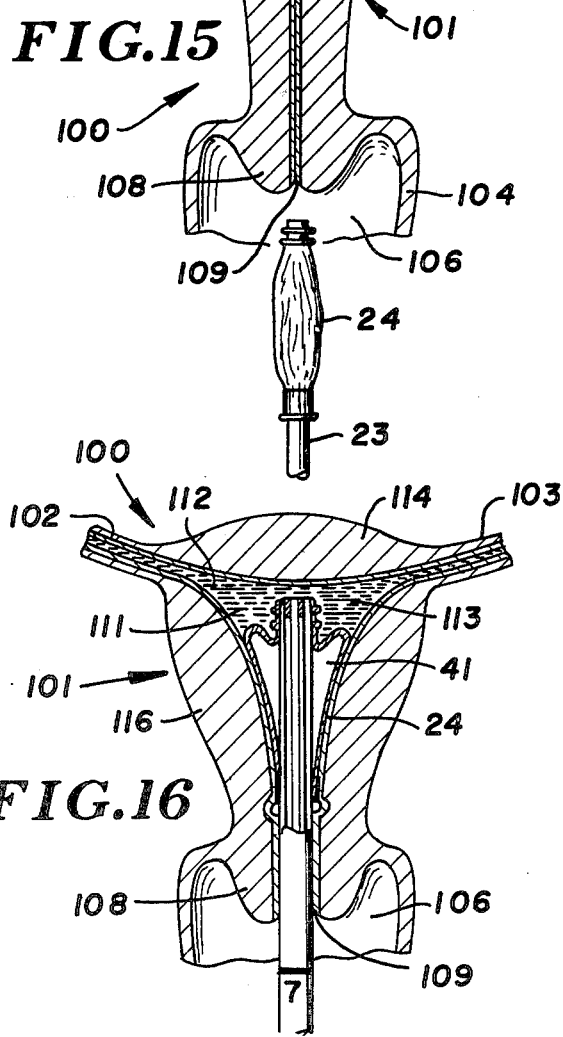
FIG. 15
FIG. 17
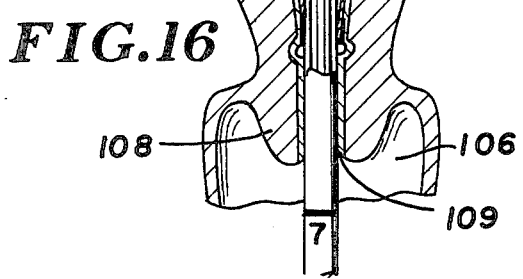
FIG. 16

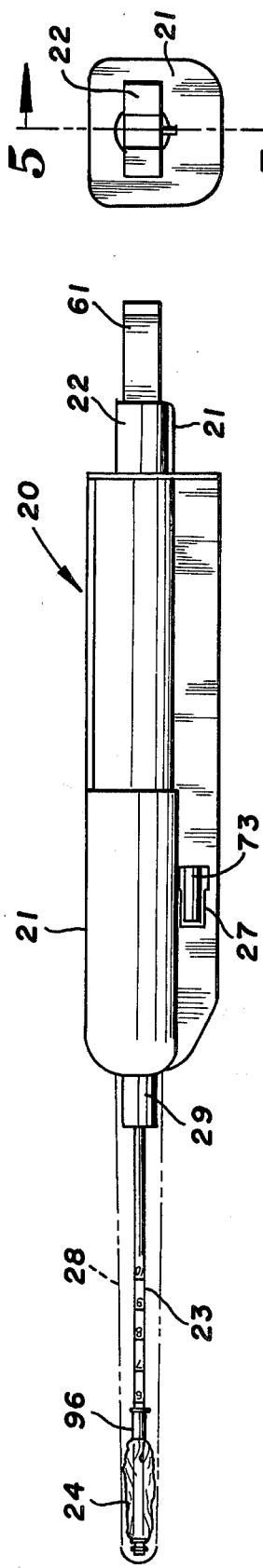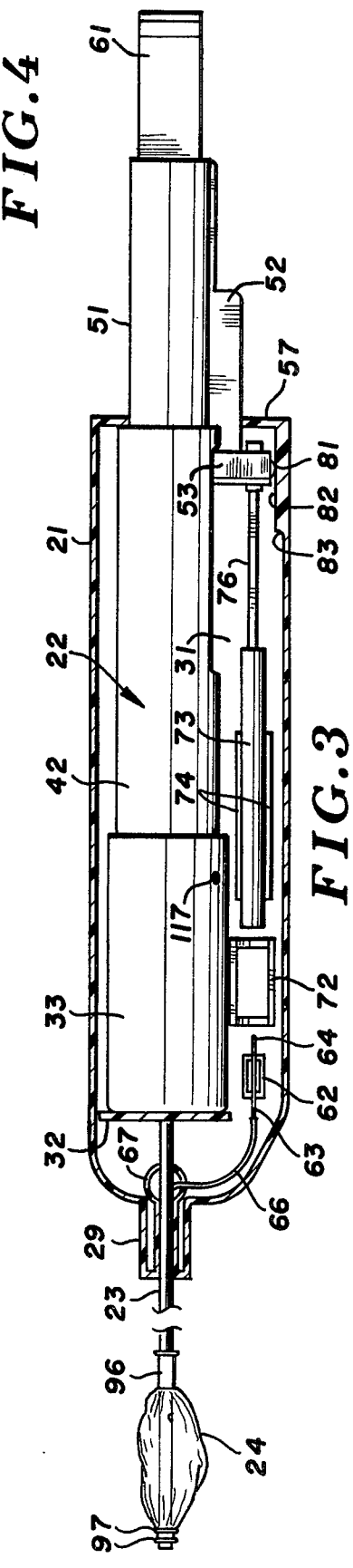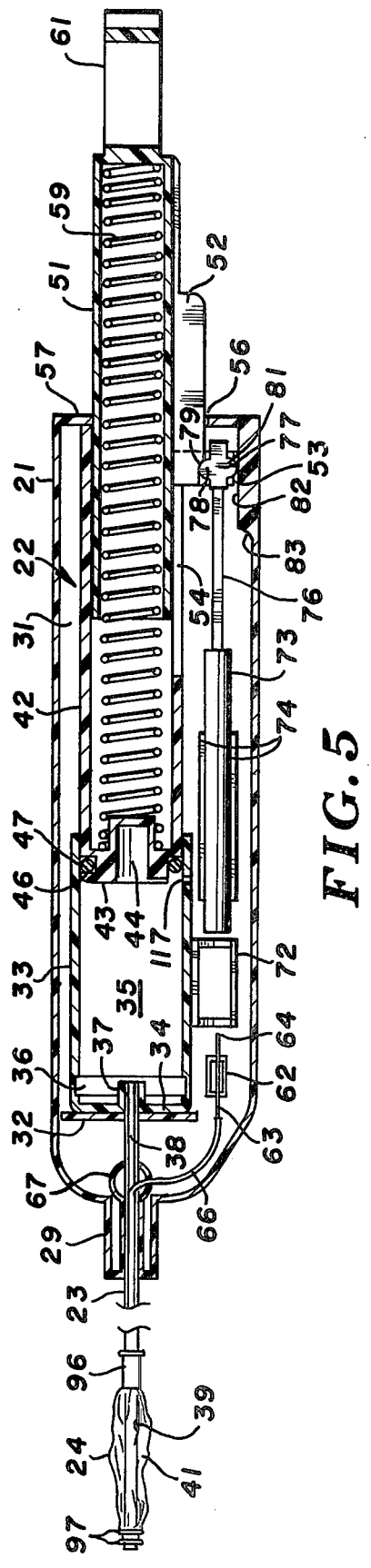

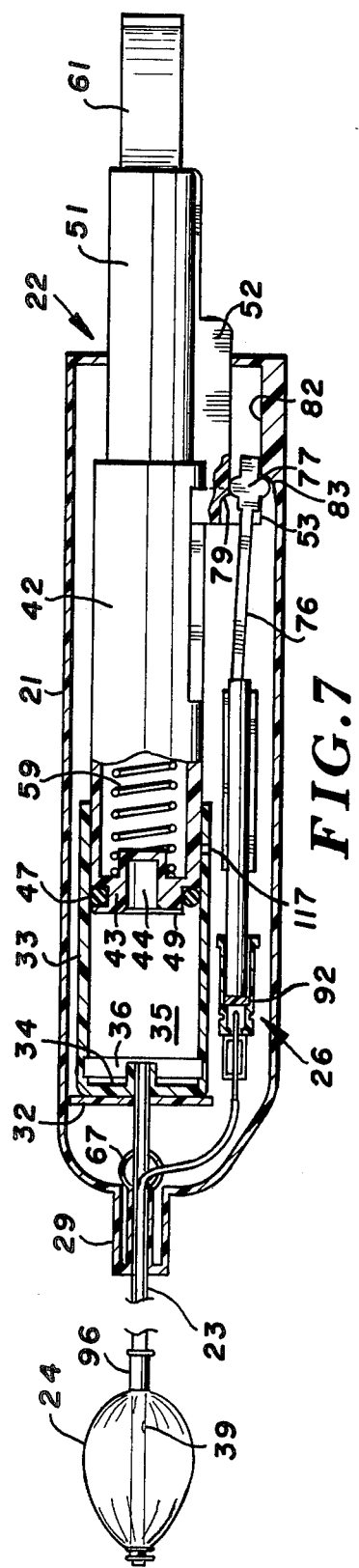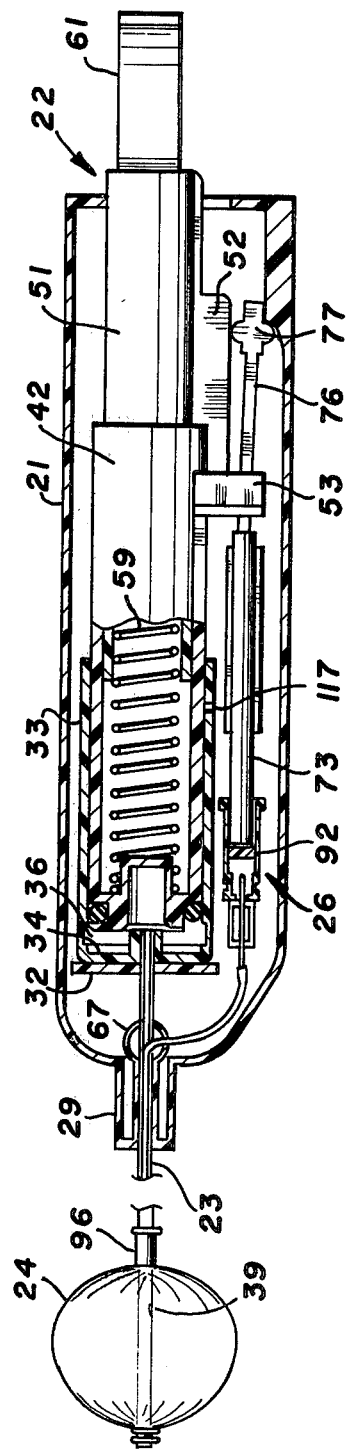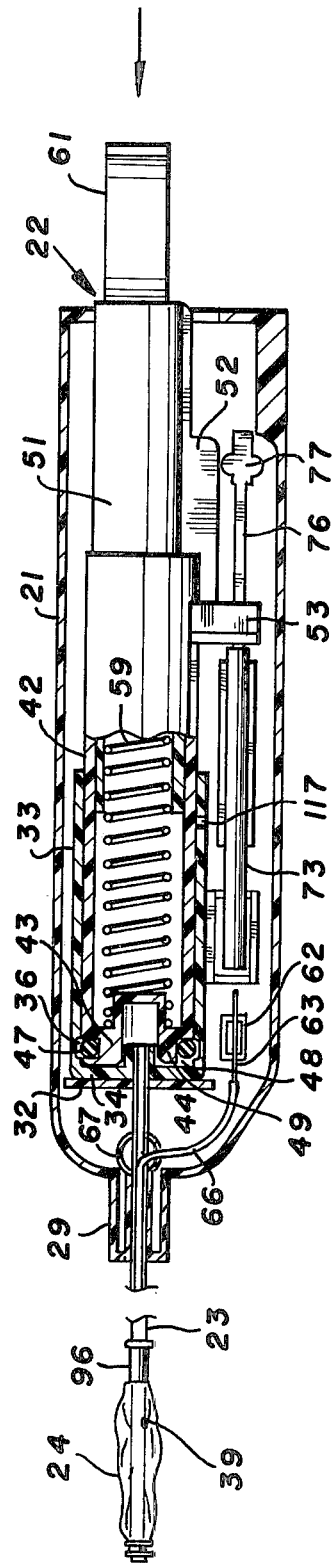

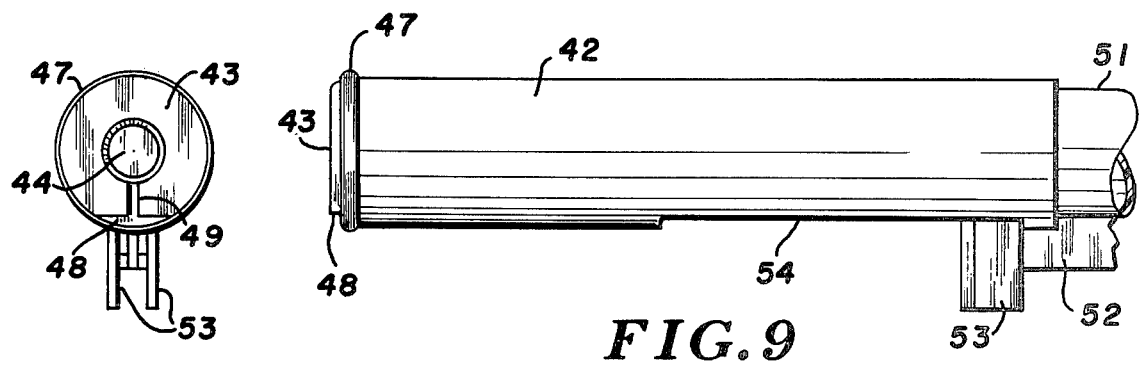
FIG.9  FIG.10
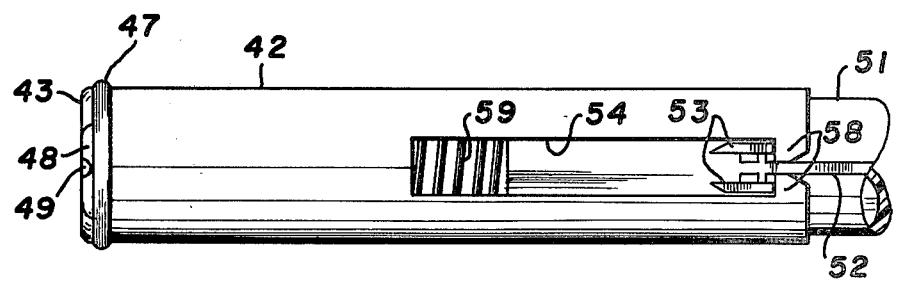
FIG.11
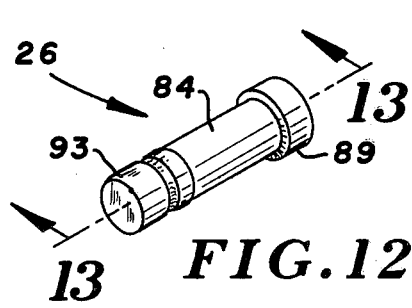
FIG.12
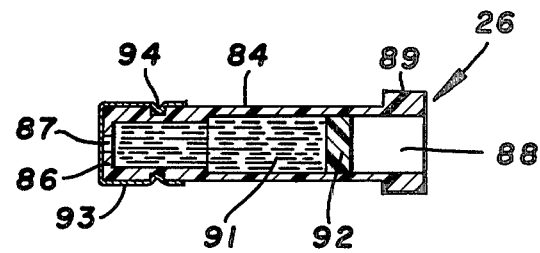
FIG.13
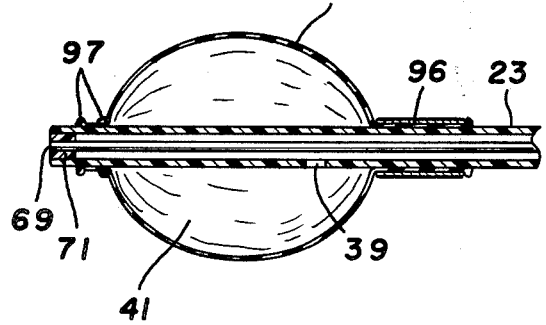
FIG.14
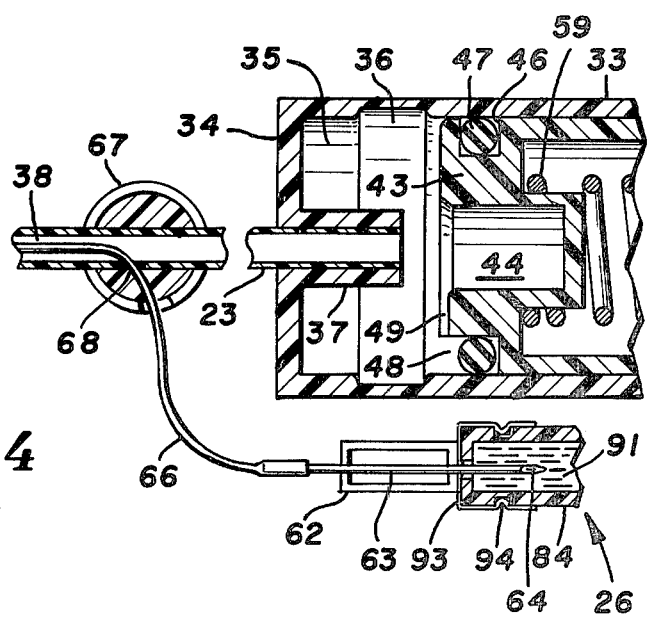

DISPENSING INSTRUMENT AND METHOD

BACKGROUND OF INVENTION

Dispensing instruments and methods of introducing fluids and fluid-like materials, as drug material, into the canals of Fallopian tubes are disclosed by Bolduc and Dickhudt in U.S. Pat. Nos. 3,822,702, 3,871,374, 3,875,939, and 3,948,259. These instruments have elongated probes with a forward end carrying expandable balloon assemblies. Dispensing structure located within the housings are used to expand the balloon assemblies and discharge drug material into the uterine cavity. The drug material to be discharged into the uterine cavity is stored in a container accommodated by the dispensing structure. In the use of these dispensing instruments, it is found that the cervices of females have different sizes and strengths. Also, the uterine cavities have different shapes and elongated sections leading to the canals of the Fallopian tubes. Under certain circumstances, it is difficult to insert the balloon assembly through the cervical opening into the uterine cavity. The tight relationship between the balloon assembly and the cervical opening causes any air that is located in the balloon assembly to expand, increasing the difficulty of inserting the balloon assembly through the cervical opening into the uterine cavity.

SUMMARY OF INVENTION

The invention is directed to an apparatus and method for dispensing fluid and fluid-like materials, as a drug material, into the canals of the Fallopian tubes of a primate female. The instrument has a housing carrying an elongated flexible probe. An expandable cylindrical balloon or sleeve attached to the outer end of the probe is used to move material dispensed in the uterine cavity into the canals of the Fallopian tubes. A piston and cylinder assembly operably associated with the housing is used to partially expand the balloon, dispense the material into the uterine cavity, and then fully expand the sleeve to move the material from the uterine cavity into the canals of the Fallopian tubes. The piston and cylinder assembly has a piston that is slidably located within a cylinder. The piston and cylinder have coacting means operable to vent air from the sleeve chamber when the piston is in its first full in position and establish a vacuum force on the balloon when the piston is moved away from the first position to fully collapse the sleeve on the probe. The fully collapsed sleeve is inserted through the cervical opening into the uterine cavity. This insertion is facilitated as the sleeve has a minimum annular size and there is no air to expand the sleeve as it is inserted through the cervical opening into the uterine cavity. Once the sleeve is inserted into the uterine cavity, the container containing the material is loaded into the instrument. The instrument is then operated to initially partially expand the sleeve, introduce the material into the uterine cavity, and then fully expand the sleeve to move the material from the uterine cavity into the canals of the Fallopian tubes. Substantially all of the material introduced into the uterine cavity is moved by the expanding sleeve into the canals of the Fallopian tubes in a short period of time. When the material like a tissue adhesive is placed in the canals, it reacts with the tissue to polymerize the adhesive and thereby occludes the canals. After the material has been moved into the canals of the Fallopian tubes, the sleeve is collapsed so that the probe and balloon can be readily withdrawn from the uterine cavity.

IN THE DRAWINGS

FIG. 1 is a perspective view of the dispensing instrument of the invention and an ampulla usable with the instrument;

FIG. 2 is a top plan view of the dispensing instrument of FIG. 1 in its storage and shipping condition;

FIG. 3 is a plan view of the dispensing instrument with the top housing removed and the piston of the piston and cylinder assembly in the out position;

FIG. 4 is an end elevational view of the right end of FIG. 2;

FIG. 5 is an enlarged sectional view taken along line 5—5 of FIG. 4 with the piston of the piston and cylinder assembly in the out position;

FIG. 6 is a view similar to FIG. 3, partly sectioned with the piston of the piston and cylinder assembly in the full in position;

FIG. 7 is a view similar to FIG. 6 with the piston of the piston and cylinder assembly located in an intermediate position;

FIG. 8 is a view similar to FIG. 6 with the piston and cylinder assembly located in the in material dispensing position;

FIG. 9 is an enlarged side view of the piston of the piston and cylinder assembly;

FIG. 10 is an end view of the left end of FIG. 9;

FIG. 11 is a bottom view of FIG. 9;

FIG. 12 is a perspective view of the ampulla;

FIG. 13 is an enlarged sectional view taken along line 13—13 of FIG. 12;

FIG. 14 is an enlarged foreshortened sectional view of the piston and cylinder assembly and balloon attached to the probe;

FIG. 15 is a sectional view of the female reproductive system prior to the insertion of the probe into the uterine cavity;

FIG. 16 is a view similar to FIG. 15 with the probe inserted into the uterine cavity and the balloon partially expanded; and FIG. 17 is a view similar to FIG. 16 with the balloon fully expanded.

DESCRIPTION OF PREFERRED EMBODIMENT

Referring to the drawing, there is shown in FIG. 1 the material dispensing instrument of the invention indicated generally at 20 operable to transfer fluid and fluid-like materials, as drug materials, into both canals of the Fallopian tubes of a reproductive system of a female. Instrument 20 has a housing or casing 21 accommodating a piston and cylinder assembly 22. An elongated flexible probe 23 is secured to and extends away from the forward end of housing 21 generally along the longitudinal axis of the housing. An expandable balloon or cylindrical sleeve 24 is mounted on the forward end of probe 23. Sleeve 24 is an expandable elastic tubular sheet member attached at its opposite ends to the probe. The material to be dispensed by the instrument is stored in an ampulla or container 26. Housing 21 has a T-shaped opening 27 to facilitate the correct loading of the ampulla 26 into the instrument. Ampulla 26 can only be loaded in one position in the instrument.

Referring to FIG. 2, sleeve 24 is shown in a contracted position. An elongated cylindrical cover 28 shown in broken lines is located over sleeve 24 and probe 23 to protect and maintain the sterile condition of the sleeve and probe. The open end of cover 28 is mounted on an annular shoulder 29 secured to the forward end of housing 21. Cover 28 is a shipping guard which encloses sleeve 24 and probe 23. Assembly 22, as shown in FIG. 2, is located in the shipping position, which prevents entrance of air into the chamber 41 surrounded by sleeve 24.

As shown in FIGS. 3 and 5, housing 21 has an inside chamber or cavity 31 accommodating piston and cylinder assembly 22. The forward end of assembly 22 bears against a fixed transverse wall 32 adjacent the forward end of housing 21. Assembly 22 includes a cylinder 33 having a closed forward end or bottom wall 34 surrounding a cylinder chamber 35. The inside side wall of cylinder 33 adjacent wall 34 has an annular pressure release groove 36, the function of which will be hereinafter described. A short cylindrical boss 37 extends inwardly from the center of wall 32. The inner end of probe 23 is mounted in boss 37 and provides an air passage 38 from cylinder chamber 35 to the chamber 41 surrounded by sleeve 24. The outer end of probe 23 has one or more holes 39 providing access for the flow of air from passage 38 into the sleeve chamber 41 formed by sleeve 24.

Assembly 22 also includes a piston 42 slidably located in cylinder 33. Piston 42 has a closed forward end or head 43. Head 43 has a forwardly open bore or recess 44 for accommodating boss 37 when the piston 42 is in the full in position. Head 43 also has an annular outwardly open groove 46 accommodating a sealing or O-ring seal 47. As shown in FIGS. 10 and 11, the face of head 43 has a recess or cut-out segment 48 open to the groove 46 and a short radial vent passage 49 connecting recess 44 to the annular groove 46. Cut-out segment 48 and passage 49 connecting recess 44 to the annular groove 46. Cut-out segment 48 and passage 49 provides an air passage between recess 44 and seal groove 46.

Returning to FIGS. 3 and 5, an actuator 51 having an elongated cylindrical tubular body is slidably located within piston 42. As shown in FIGS. 5, 9, and 11, an elongated longitudinal rib 52 extends downwardly from actuator 51. The forward end of rib 52 is connected to a pair of downwardly directed ears 53. The ears 53 extend through a longitudinal slot 54 in the bottom of side of piston 42. Actuator 51 projects through a hole 56 in the rear end wall 57 of housing 21. Actuator 51 is movable into the housing 21 to move the piston 42 to a first full in position close to the bottom of cylinder 33. As shown in FIG. 11, piston 42 has a pair of inwardly directed lips 58 located adjacent opposite sides of rib 52. Lips 58 are engaged by ears 53 to limit the outward movement of actuator 51 relative to piston 52. A coil spring 59 located longitudinally within piston 52 and actuator 51 biases piston 52 and actuator 51 in opposite directions. Lips 58 function as stops to hold piston 52 and actuator 51 in their relative extended positions.

A finger ring 61, shown in FIGS. 1, 2, and 4, is integral with the rear or outside end of actuator 51. Ring 61 is used by the hand of the operator to move the actuator 51 into and out of housing 21 during the dispensing procedure.

As shown in FIGS. 5 and 14, a support 62 located adjacent wall 32 carries a longitudinal tubular needle 63. Needle 63 has a sharp forward or inlet end 64. The opposite end of needle 63 is connected to a tube or hose 66. Hose 66 extends through a post or support 67 integral with the forward end of housing 21. Post 67 also supports probe 23. Tube 66 extends through a closed hole 68 into passage 38 of probe 23. The outlet end 69 of tube 66 is mounted in a plug 71 fitted into the remote or forward end of probe 23. Plug 71 also closes the air passage 38 of probe 23. A cradle or holder 72 for accommodating ampulla 26 is located immediately in front of the needle point 64. Cradle 72 is integral with a portion of housing 21 and faces the loading opening 27 in housing 21.

As shown in FIGS. 3 and 5, an elongated linear push rod 73 is slidably mounted for linear movement between a pair of ribs 74 integral with housing 21. Push rod 73 is in general longitudinal alignment with needle 63 and functions to move the ampulla 26 into the needle 63 and forces the material stored in the ampulla through the needle 63 and tube 66 and out outlet end 69. Push rod 73 is integral with a linear flexible neck 76. The neck 76 terminates in head 77 that cooperates with actuator 51 to control the movement of push rod 73. Head 77 has a first ear 78 located in a notch 79 in rib 52 between ears 53. Head 77 has a second ear 81 that extends in a direction opposite the first ear 78 and rides on a linear edge 82 on the inside wall of housing 21. Edge 82 has a forward shoulder 83 for accommodating ear 81 on inward movement of actuator 51 and piston 42. This structure is defined in Applicant's copending U.S. Application Ser. No. 713,294 filed Aug. 10, 1976 now U.S. Pat. No. 4,109,654. The structure of this Application is incorporated herein by reference.

Referring to FIGS. 1, 12, and 13, ampulla 26 has a cylindrical side wall 84 integral with an end wall 86. The center of end wall 86 has a hole 87 to accommodate the forward end of needle 63. The opposite end of the side wall 84 is open and surrounded by a large radially outwardly directed portion or flange 89. The material 91 to be dispensed, as drug material, is located in the chamber surrounded by side wall 84. A movable plug or piston 92 is located in a sealing relationship with the inside wall of side wall 84 which stores the material 91 in the ampulla. The forward end of 86 is sealed with a foil seal member such as metal foil 93. The foil 93 extends outside of the side wall 84 into an annular groove 94. Flange 89 on side wall 84 has an outside diameter that is larger than the narrow portion of T-slot 27 in housing 21. Flange 89 fits through the enlarged portion of the T-slot. This prevents the ampulla 26 from being loaded backwards into the instrument.

As shown in FIG. 14, probe 23 is an elongated flexible tubular member. Preferably probe 23 is a plastic member having visual indicia marks indicating the insert position of sleeve 24 in the uterine cavity. Balloon or sleeve 24 is a flexible, elastic and expandable cylindrical sheet member or rubber or rubber-like material. The inner end of the sheet member is clamped within a sealing relationship about the probe 23 with an annular sleeve 96. The outer end of sleeve 24 is sealed to the tip of probe 23 with a pair of annular sealing members 97, as clamp cords or the like.

Referring to FIG. 15, there is shown a female reproductive system indicated generally at 100 of a primate female for receiving the sleeve end of probe 23. The reproductive system 100 has a uterus 101 joined to a pair of Fallopian tubes 102 and 103. The lower part of uterus 101 is integral with an elongated vagina 104. Vagina 104 has a vaginal cavity 106 and an entrance or vestibule 107. The opposite end of vaginal cavity 106 is in communication with the cervix 108. The cervix 108 has a normally closed exit opening 109 providing a passage from vaginal cavity 106 to the uterine cavity 111. The Fallopian tubes 102 and 103 have passages which exit at 112 and 113 into the uterine cavity 111.

Uterus 101 is a generally pear-shaped, thick walled, hollow organ. The uteri of females vary in size and shape. Wall thickness, wall strength and sensitivity to pain varies from female to female. Also, the size and configuration of the uterine cavity 111 varies in females. The uterine cavity 111 is generally flat and triangular in shape. Other sizes and shapes of the uterine cavities have been noted. The exit sections of the canals 112 and 113 open to the uterine cavity 111 may be enlarged and elongated and are in effect an extension of the uterine cavity. Uterus 101 has a top wall or fundus 114 and side walls 116 which lead to the cervix 108. The cervix's muscles of females vary in strength and size so that in some cases the insertion of probe 23 through the cervical opening encounters some resistance. Sleeve 24 has an elongated loose shape so that it can fully expand and move the material dispensed in the uterine cavity through the elongated exit sections of the canals and into the narrow sections of the canals.

In use, referring to FIG. 2, the instrument 20 is packaged for shipment with cover 28 located over probe 23 and sleeve 24. The patient is prepared for treatment by the attending personnel. The cover 28 is removed from probe 23 to expose sleeve 24. The push rod 73 is located over the cradle 72 in front of the opening 27. This prevents the loading of the ampulla 26 in the instrument. The air that may be trapped in the sleeve 24 is evacuated or vented from the sleeve chamber 41 by pushing actuator 51 into housing 21. As shown in FIG. 6, when actuator 51 is in its full in or first position, piston 42 is bottomed on or in engagement with wall 34. This locates O-ring seal 47 in alignment with annular groove 36 on the inside of cylinder 33 out of sealing engagement with cylinder 33. The air in sleeve 24, as well as passage 38 of probe 23, flows through recess 44 to vent passage 49 past the O-ring seal 47 and piston 42 to atmosphere. Actuator 51 is then retracted from housing 21 moving piston 42 away from wall 34. This establishes a vacuum force on sleeve 24 collapsing it into tight engagement with the end of probe 23. The vacuum force is established because O-ring seal 47 moves out of groove 36 into sealing engagement with the inside wall of cylinder 33. The instrument is now ready for insertion of sleeve 24 through cervix opening 109 and into uterine cavity 111.

Referring to FIG. 16, sleeve 24 has been inserted through cervical opening 109 and is located in uterine cavity 111. Sleeve 24 and probe 23 can be rotated about the longitudinal axis of the probe during the insertion procedure. This facilitates the slipping of the sleeve through cervical opening 109. The entire instrument is rotated in opposite directions to twist the sleeve 24 in opposite directions. Once sleeve 24 is in uterine cavity 111, the actuator 51 is moved to its full out or second position as shown in FIG. 5. Piston 42 is moved to the outer end of cylinder 33 locating the O-ring seal 47 outwardly of a small vent hole 117. With piston 42 in the full out position, air flows into cylinder chamber 36 through hole 117.

The push rod 73 is also moved to a rearward position. This is accomplished by the ears 53 which engage the head 77. Head 77 is moved on housing edge 82 and in notch 79 of rib 52. This locates push rod 73 out of alignment with opening 27 so that the ampulla 26 can be loaded into the instrument 20.

Ampulla 26, containing the drug material, is now located in the cradle 72. This is accomplished by inserting the ampulla through the opening 27. The enlarged flange or head 89 of the ampulla only fits through the enlarged portion of T-slot 27. The cradle 72 longitudinally aligns the open end 88 of the ampulla with the forward end of the push rod 73. The forward end of ampulla 26 is in longitudinal alignment with the needle 63.

Referring to FIG. 7, actuator 51 has been partially moved into the housing 21. This movement moves piston 42 into cylinder 33. This partially expands sleeve 24. During the expansion of sleeve 24 push rod 73 moves toward ampulla 26. The forward end of push rod 23 engages movable plug 92 and forces the ampulla into needle 63 after partial expansion of sleeve 24. The forward or sharp end 64 of the needle 63 pierces the foil covering 93 and the ampulla bears against the support 62. The continued movement of the push rod 73 moves plug 92 relative to the cylinder 84 thereby forcing the material 91 through needle 63, tube 66, and into the upper portion of the uterine cavity. The drive connection between head 77 and rib 52 is maintained by notch 79 and the linear edge 82 of housing 21. As soon as the head 77 reaches shoulder 83 it is forced downwardly out of the notch 79 thereby terminating the longitudinal movement of push rod 73. The actuator 51 is free to continue to be moved in an inward direction to fully expand sleeve 24 to pump the material into the canals of the Fallopian tubes.

As shown in FIG. 8, actuator 51 has been moved into its full in position with sleeve 24 in its full expanded position. FIG. 17 shows the sleeve 24 located in the uterine cavity 111 with material forced into canals 112 and 113 of the Fallopian tubes 102 and 103. The expanding sleeve, being flexible, conforms to the shape of the inside of the uterine wall. The uterine wall 116, being a heavy muscle, counteracts the expansion forces of the expanding sleeve 24 and thereby affects the pushing or pumping action of the material into the canals 112 and 113 of the Fallopian tubes 102 and 103.

Sleeve 24 is collapsed by withdrawing actuator 51 from housing 21. This moves piston 42 out of cylinder 33 thereby establishing a vacuum force in the cylinder chamber 35. This quickly collapses sleeve 24. Sleeve 24 and probe 23 is then readily retracted from the uterine cavity and the patient.

The drug material moved into the canals of the Fallopian tubes can be the drug materials identified in Applicant's U.S. Pat. No. 3,948,259. These materials include tissue adhesives, contraceptive drugs, biologicals, diagnostic materials, anaesthetic materials, as well as drugs which enhance the fertilization and conception of the female. The drug materials identified in U.S. Pat. No. 3,948,259 are incorporated in this disclosure.

While there have been shown and described the preferred embodiment of the dispensing instrument and method of introducing material into the canals of the Fallopian tubes of the female, it is understood that various changes in the structure and method may be made by those skilled in the art without departing from the invention.

The embodiments of the invention in which an exclusive property or privilege is claimed are defined as follows:

1. An instrument for placing material into both canals of the Fallopian tubes of a female comprising: an expandable member positionable in the uterine cavity;

dispensing means positionable in the uterine cavity for supporting said expandable member and for dispensing material between said expandable member and the walls of the uterine cavity; and means for collapsing said expandable member against said dispensing means before introduction of the expandable member through the cervical opening into the uterine cavity and for expanding the expandable member in the uterine cavity to move material from the uterine cavity to the canals of the Fallopian tubes.

2. The instrument of claim 1 wherein said collapsing means further comprises: means for subjecting said expandable member to a vacuum force for collapsing said expandable member against said dispensing means.

3. An instrument for placing material into both canals of the Fallopian tubes of a female comprising: an expandable member positionable in the uterine cavity; dispensing means positionable in the uterine cavity for supporting said expandable member and for dispensing material between said expandable member and the walls of the uterine cavity; and means for collapsing said expandable member against said dispensing means for allowing introduction and removal of the expandable member through the cervical opening into and from the uterine cavity, said means for collapsing said expandable member including actuator means coupled with said dispensing means and said expandable member selectively operable in sequence to fully collapse and then partly expand said expandable member, dispense said material through said dispensing means and further expand said expandable member to move said material from the uterine cavity into the canals of the Fallopian tubes.

4. The instrument of claim 3 further comprising:
a housing having a cavity and a forward end, and an elongated tubular probe having a forward end adapted to be placed in the uterine cavity and secured to the forward end of the housing;
and wherein:
said dispensing means comprises said elongated tubular probe;
said expandable member comprises expandable sleeve means surrounding a sleeve chamber mounted on the forward end of said probe; and
said actuator means comprises a piston and cylinder assembly located within the cavity operable to supply air to the sleeve chamber to expand the sleeve means, said piston and cylinder assembly having a cylinder defining a cylinder chamber, said probe being connected to the cylinder, said probe having a passage connecting the cylinder chamber with the sleeve chamber, a piston movable into the cylinder chamber to move air from the cylinder chamber through the probe passage into the sleeve chamber thereby expanding the sleeve means, said piston and cylinder having coacting means operable to vent the sleeve chamber when the piston is moved to a first position and to subject the sleeve chamber to a vacuum force when the piston is moved away from the first position toward a secured position thereby collapsing the sleeve means about the probe to facilitate insertion of the sleeve means and forward end of the probe through the cervical opening and into the uterine cavity, and means operably connected to the piston and cylinder assembly to dispense material from a container storing the material into a tubular line extended through the passage of the probe and open at the forward end of the probe for discharge into the uterine cavity.

5. The instrument of claim 4 wherein: the cylinder has a bottom wall and a cylindrical side wall surrounding the cylinder chamber, said coacting means of the piston and cylinder comprising an annular groove on the inside of the cylindrical side wall adjacent the bottom wall, an annular seal mounted on the piston in normal sealing engagement with the cylinder side wall, and passage means on the piston connecting the seal with the area of the piston located adjacent the passage in the probe, said seal being located in said annular groove out of sealing engagement with the cylindrical side wall when the piston is in its first position in close proximity with the bottom wall whereby air from sleeve chamber is vented past said annular seal.

6. The instrument of claim 5 wherein: the piston has an outwardly open annular groove accommodating the annular seal.

7. The instrument of claim 6 wherein: the passage means on the piston connects the groove on the piston with the center area of the piston.

8. The instrument of claim 5 wherein: the annular seal is an O-ring.

9. The instrument of claim 4 including: actuator means operably connected to the piston and extended away from the housing, said actuator means being movable to move the piston relative to the cylinder.

10. The instrument of claim 9 including: biasing means between the actuator means and piston providing yieldable compression link between the actuator means and piston when the actuator means is moved into the housing to move the piston to its in position.

11. The instrument of claim 4 wherein: the coacting means of the piston and cylinder comprise a groove on the cylinder open to the cylinder chamber, a seal on the piston in normal sealing engagement with the cylinder, said seal being located in said groove out of sealing engagement with said cylinder when the piston is in its first position whereby air from the chamber of the expandable means is vented past said seal, said piston on movement from its first position to its second position moves the seal out of the groove into sealing relation with the cylinder whereby a vacuum force is applied to the expandable means.

12. The instrument of claim 11 wherein: the groove is an annular groove in the cylinder and the seal is an annular seal.

13. The instrument of claim 12 wherein: the piston has an outwardly open annular groove accommodating the annular seal.

14. The instrument of claim 13 wherein: the piston has a passage means connecting the groove on the piston with the center area of the piston.

15. The instrument of claim 13 wherein: the annular seal is an O-ring.

16. An instrument for moving material from a container having an enlarged portion to a uterine cavity and placing the material into both canals of the Fallopian tubes of a female comprising: a housing having an inside cavity, an elongated tubular probe mounted on the housing, an expandable sleeve means surrounding a sleeve chamber mounted on the probe, means for supplying a fluid to the sleeve chamber to expand the sleeve means, holder means in the cavity for accommodating the container having an enlarged portion, said housing having an opening complimentary in shape to the shape of the container whereby the container can only be loaded in one position in the holder means, and means operable to move the material from the container to the uterine cavity.

17. The instrument of claim 16 wherein: the opening in the housing has a general T-shape, said container having an enlarged end adopted to only pass through the enlarged part of the T-shaped opening.

18. The instrument of claim 16 wherein: said means operable to move the material from the container includes a fixed tubular needle mounted adjacent the holder means, tubular means connected to the needle and extended through the tubular probe, said tubular means having a discharge end at the end of the probe, and a plunger operable to move the container into the needle and force the material in the container through the needle and tubular means to the uterine cavity.

19. The instrument of claim 16 wherein: the means for supplying a fluid to the sleeve chamber is a piston and cylinder assembly located within the cavity, said piston and cylinder assembly having a cylinder defining a cylinder chamber open to the tubular probe, and a piston movable into the cylinder chamber, said piston and cylinder having coacting means operable to vent fluid from the sleeve chamber when the piston is moved to a first position in the cylinder and to subject the sleeve means to a vacuum force when the piston is moved from the first position to a second position thereby facilitating the insertion of the sleeve means through the cervical opening leading to the uterine cavity.

20. The instrument of claim 19 wherein: the cylinder has a bottom wall and a cylindrical side wall surrounding the cylinder chamber, said coacting means of the piston and cylinder comprising an annular groove on the inside of the cylindrical side wall adjacent the bottom wall, an annular seal mounted on the piston in normal sealing engagement with the cylinder side wall, and passage means on the piston connecting the seal with the area of the piston located adjacent the passage in the probe, said seal being located in said annular groove out of sealing engagement with the cylindrical side wall when the piston is in its first position in close proximity with the bottom wall whereby fluid from sleeve chamber is vented past said annular seal.

21. The instrument of claim 20 wherein: the piston has an outwardly open annular groove accommodating the annular seal.

22. The instrument of claim 21 wherein: the passage means on the piston connects the groove on the piston with the center area of the piston.

23. The instrument of claim 21 wherein: the annular seal is an O-ring.

24. The instrument of claim 19 including: actuator means operably connected to the piston and extended away from the housing, said actuator means being movable to move the piston relative to the cylinder.

25. The instrument of claim 24 including: biasing means between the actuator means and piston providing a yieldable compression link between the actuator means and piston when the actuator means is moved into the housing to move the piston to its in position.

26. A piston and cylinder assembly for selectively expanding and collapsing an expandable means having a chamber comprising: a cylinder having a cylinder chamber adapted to be connected to the chamber of the expandable means, a piston movable into the cylinder chamber to force air out of the cylinder chamber and into the chamber of the expandable means to expand the expandable means, said piston being movable between a first in position and a second out position relative to the cylinder, said piston and cylinder having coacting means operable to vent the chamber of the expandable means when the piston is in its full in position and subject the expandable means to a vacuum force when the piston is moved from the full in position to the out position.

27. The instrument of claim 26 wherein: the coacting means of the piston and cylinder comprise a groove on the cylinder open to the cylinder chamber, a seal on the piston in normal sealing engagement with the cylinder, said seal being located in said groove out of sealing engagement with said cylinder when the piston is in its first position whereby air from the chamber of the expandable means is vented past said seal, said piston on movement from its first position to its second position moves the seal out of the groove into sealing relation with the cylinder whereby a vacuum force is applied to the expandable means.

28. The instrument of claim 27 wherein: the groove is an annular groove in the cylinder and the seal is an annular seal.

29. The instrument of claim 28 wherein: the piston has an outwardly open annular groove accommodating the annular seal.

30. The instrument of claim 29 wherein: the piston has a passage means connecting the groove on the piston with the center area of the piston.

31. The instrument of claim 29 wherein: the annular seal is an O-ring.

32. A method of placing material in both canals of Fallopian tubes open to the uterine cavity of a uterus with an expandable sleeve mounted on a probe and surrounding a sleeve chamber comprising: applying a vacuum pressure to the sleeve chamber to collapse the sleeve onto the probe, inserting the collapsed sleeve and probe through the cervical opening to locate the sleeve and probe in the uterine cavity, partially expanding the sleeve into engagement with the inside walls of the uterus, discharging material into the uterine cavity between the partially expanded sleeve and top wall of the uterus, further expanding the sleeve to fill the uterine cavity thereby moving the material in the uterine cavity into the canals of the Fallopian tubes, contracting the sleeve, and removing the contracted sleeve and probe from the uterine cavity.

33. The method of claim 32 including: venting air from the sleeve chamber before the vacuum pressure is applied to the sleeve chamber.

34. The method of claim 32 wherein: the collapsed sleeve and probe are rotated along the longitudinal axis of the probe during the insertion thereof through the cervical opening.

35. The method of claim 32 wherein: the sleeve is contracted by subjecting the sleeve chamber to a vacuum pressure.

* * * * *